(12) United States Patent
Kon et al.

(10) Patent No.: US 7,904,172 B2
(45) Date of Patent: Mar. 8, 2011

(54) PROGRAMMABLE APPARATUS AND METHOD FOR OPTIMIZING AND REAL TIME MONITORING OF GENE TRANSFECTION BASED ON USER CONFIGURED ARBITRARY WAVEFORM PULSING TRAIN

(75) Inventors: Oi Lian Kon, Singapore (SG); Mohamad Pauzi Bin Hussen, Eunosville (SG); Steven Teck Boon Yap, Singapore (SG)

(73) Assignee: Nanyang Polytechnic, Singapore (SG)

( * ) Notice: Subject to any disclaimer, the term of this patent is extended or adjusted under 35 U.S.C. 154(b) by 1649 days.

(21) Appl. No.: 11/171,451

(22) Filed: Jul. 1, 2005

(65) Prior Publication Data
US 2006/0142688 A1  Jun. 29, 2006

(30) Foreign Application Priority Data
Dec. 28, 2004  (SG) ............... 200407948-9

(51) Int. Cl.
*A61N 1/30* (2006.01)

(52) U.S. Cl. ............ 607/72; 607/3; 607/96; 607/98; 607/99; 607/108; 607/115; 604/20; 604/21; 435/173.6

(58) Field of Classification Search ......... 607/3, 72, 607/96–99, 108, 115; 604/20–21; 435/173.6
See application file for complete search history.

(56) References Cited

U.S. PATENT DOCUMENTS
3,727,616 A * 4/1973 Lenzkes ............... 607/59
* cited by examiner

*Primary Examiner* — Carl H Layno
*Assistant Examiner* — Deborah Malamud
(74) *Attorney, Agent, or Firm* — Pyprus Pte Ltd

(57) ABSTRACT

The present invention provides an apparatus and a method for generating and applying an electric field according to a user configured arbitrary waveform pulsing train. A control module allows the user to input operation parameters and configure the arbitrary waveform pulsing train for the electroporation process. A micro-controller unit coupled to the control module controls an arbitrary waveform generator unit and a customized power module. During the electroporation process, the arbitrary waveform generator unit produces the arbitrary waveform pulsing train that is amplified by the customized power module. The customized power module is coupled to at least two electrodes, wherein the at least two electrodes will produce an electric field across a target media.

7 Claims, 2 Drawing Sheets

PROGRAMMABLE APPARATUS AND METHOD FOR OPTIMIZING AND REAL TIME MONITORING OF GENE TRANSFECTION BASED ON USER CONFIGURED ARBITRARY WAVEFORM PULSING TRAIN

FIELD OF THE INVENTION

The present invention relates to the field of electroporation, gene transfection and cell fusion. More particularly, the invention concerns an electroporation apparatus and method for generating and applying an optimized electric field according to user configured arbitrary waveform pulsing trains to efficiently and effectively introduce molecules into cells both in-vivo and ex-vivo with minimal cellular tissue damage.

BACKGROUND OF THE INVENTION

Electroporation was first discovered in the 1970s when scientists demonstrated the use of electric fields to create or induce/open pores in cells without causing permanent damage to the cells. This discovery was developed to enable the delivery of genes and various molecules into living cells, tissues and organs. By applying an electric field across cells or tissue element, the permeability of cell membrane is enhanced to enable the entry of genes and molecules into the cell cytoplasm. This phenomenon is transient as the pores reseal upon removal of the applied electric field. Presently, the application of electroporation has expanded into various diverse fields such as molecular biology, cell biology, plant genetics, hybridoma technology, agriculture research, gene therapy and others.

Applications of electroporation involve in-vivo or ex-vivo (in vitro) processes where foreign materials are introduced into living cells, tissues or organs. These living cells include human cells, mammalian cells, plant protoplasts, bacteria, fungi and others. Foreign materials, referred herein as "implant agents", to be introduced into the living cells can include but not limited to genes, DNA, peptides, proteins and other pharmacological compounds. Under in-vivo procedures, the electroporation process occurs within the living organism. Tweezer and needle electrodes are employed to secure the tissue of interest in place, for example the tumor itself and/or the epidermis encompassing the area of cells to be treated in place, while providing an electric field across the specified region of interest. Cell membranes are transiently made porous by the presence of an applied electric field, thereby allowing the implant agents to enter cells concerned, wherein the implant agents act as modifiers to the cell genome. With the ex vivo procedures, electroporation occurs in an artificially cultured environment, whereby external implant agents are introduced to the living cells. Other electrodes in the form of parallel stainless steel or platinum plates, rods or wires can be utilized to create the electric field across the target cell in ex vivo procedures. Hereinafter, the target media can refer to a living cell, a tissue element or a mixture of implant agents and living cells.

In the field of cancer treatment, for example chemotherapy, conventional methods of absorbing anti-cancer drugs by a human body are deleterious to the surrounding healthy cells. Typically, the high dosage of drugs used to eliminate the cancer cells tends to destroy a significant percentage of healthy cells. Furthermore, certain promising anticancer drugs, for example Bleomycin, have demonstrated inability to enter the membrane of cancer cells effectively. Therefore, electroporation is an excellent alternative methodology for the research of chemotherapy, known as electrochemotherapy, whereby electric pulses are used to increase the permeability of cancerous cell walls so as to allow higher concentration of anticancer drugs to penetrate the cancer cell cytosol. Application of electrochemotherapy is more beneficial to the patient as it minimizes the dosage of treatment drugs and more importantly, the anticancer drugs are able to enter the cancer cells more effectively with minimal tissue damage.

An electroporation method and apparatus generating and applying an electric field according to a user-specific pulsing scheme is taught in U.S. Pat. No. 5,869,326. FIGS. 5-9 of the U.S. patent illustrates various user-specified pulse shapes limited to "high" and/or "low" output voltages. While the user may be able to specify the range of the output voltage, the shape of pulses is limited to only rectangular waveforms. In order to achieve an effective and reliable electroporation treatment, physical parameters such as duration, strength, form and frequency of pulses must be controllable over the treatment region of interest. Hence it is imperative to achieve an apparatus and method for electroporation that can provide programmable arbitrary waveform pulsing trains for optimizing the treatment condition.

Electroporation allows the insertion of certain implant agents to selectively treat undesirable cells without damaging the surrounding healthy cells or tissues. However, the electric pulses typically used in electroporation may cause considerable discomfort and permanent side effects to patients. Major factors affecting the cell permeability induced by electroporation are dependent on important parameters, for example electric pulse strength, pulse duration, pulse shapes and pulse intervals. These physical parameters must be appropriately configured for each individual treatment, as every patient is unique, to prevent irreversible damage to the target cells due to excessive pulse strength. Ineffective opening of the pores, insufficient pulse strength and other capability limiting parameters will also affect the reliability of the treatment. Therefore, optimization of the electric field strength and pulse duration to maximize cell survival and efficient treatment is of extreme importance, and is difficult to achieve based on traditional and conventional single pulse methodologies. Furthermore, the biological properties, for example the type, size and electric conductivity of the cell, may affect the treatment result. Hence there is a need to devise an apparatus and method for generating, applying and monitoring an optimized electric field according to a user configured arbitrary waveform pulsing train.

The present invention optimizes, monitors, modifies and records all processes parameters and conditions of gene transfection, during electroporation with the provision of advanced performance capabilities and flexibilities to configure all process parameters including but not limited to pulse shape, frequency, duration, field strength and other critical important influencing factors.

SUMMARY OF THE INVENTION

The present invention provides an apparatus and method for generating and applying an optimized electric field according to user configured arbitrary waveform pulsing trains Accordingly, in one aspect, the present invention provides an apparatus for generating arbitrary waveform pulsing trains for an electroporation process, said apparatus comprising a customized power module, including a direct current (DC) power supply array for providing an output voltage; a capacitor; an electronic switch coupled to the DC power supply array, wherein the electronic switch provides means for controlling the output voltage from the DC power supply array to the capacitor; a pulse width modulation (PWM) controller coupled to the electronic switch, wherein the PWM controller receives an arbitrary waveform pulsing train and command signals for controlling the electronic switch; a low pass filter (LPF) coupled to the capacitor, wherein the LPF receives a output waveform pulsing train from the capacitor and removes high frequency spikes in the output waveform pulsing train from the capacitor, producing a filtered waveform pulsing train; a polarity switch unit coupled to the low pass filter, wherein the polarity switch unit reverses the polarity of the required pulses in the filtered waveform pulsing train to produce an amplified waveform pulsing train; a waveform generator unit coupled to the customized power module, wherein the waveform generator unit provides the arbitrary waveform pulsing train to the customized power module; and wherein the amplified waveform pulsing train produced by the polarity switch unit substantially corresponds to the arbitrary waveform pulsing train.

In another aspect, the present invention provides a method for generating an arbitrary waveform pulsing train for being used in an electroporation process comprising the steps of (a) configuring an arbitrary waveform pulsing train using a control module; (b) inputting operation parameters into the control module; (c) storing the arbitrary waveform pulsing train into an arbitrary waveform generator unit; (d) storing the operation parameters into a micro-controller unit; (e) generating first pulse of the arbitrary waveform pulsing train by the arbitrary waveform generator unit; (f) amplifying the first pulse of the arbitrary waveform pulsing train by the customized power module; (g) producing an electric field across a target media using the amplified first pulse; and (h) checking if pulses in the arbitrary waveform pulsing train are completed

BRIEF DESCRIPTION OF THE DRAWINGS

Preferred embodiments according to the present invention will now be described with reference to the drawings, in which like reference numerals denote like elements.

DETAILED DESCRIPTION OF THE INVENTION

Figure 1:
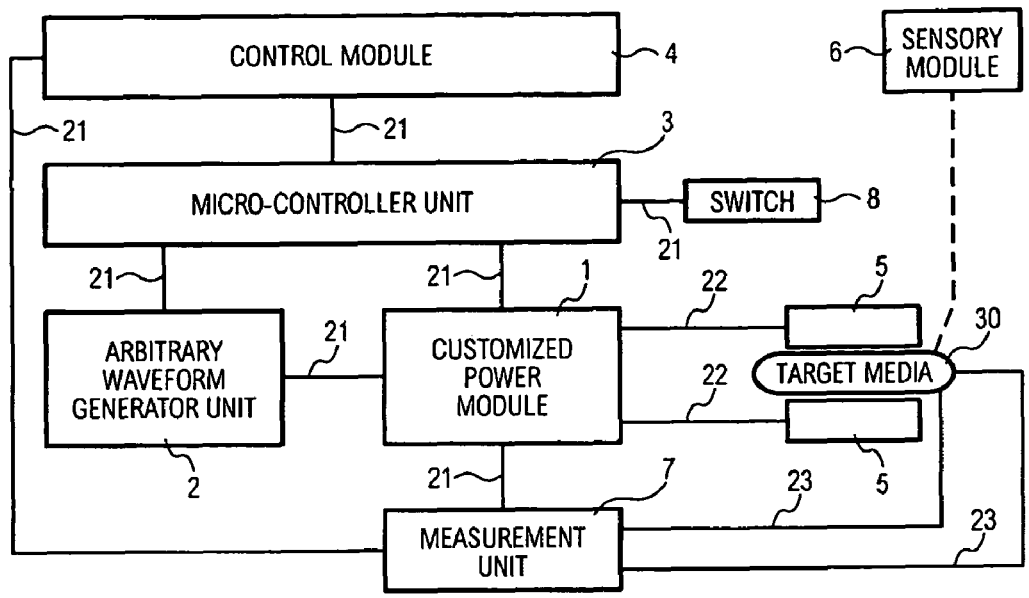
FIG. 1 illustrates a block diagram of the hardware components and interconnections of the present invention.

The present invention provides an apparatus and method for optimizing, monitoring, modifying and recording the complete electroporation process. FIG. 1 illustrates the apparatus in accordance with one embodiment of the present invention, which comprises a control module 4, a micro-controller unit 3, an arbitrary waveform generator unit 2, a customized power module 1, a measurement unit 7, a set of electrodes 5, a switch unit 8 and a sensory module 6.

The preferred embodiments of the aforesaid components in the apparatus will now be described. The control module 4 consists of a computer with keyboard, mouse and a graphic user interface (GUI) that allows a user to input, configure, program, modify, recall and store any set of desired parameters of the arbitrary waveform pulsing train for both the transient and actual programmed process. During the electroporation process, the transient conditions may deviate significantly from the actual programmed conditions. This effect is largely due to the inherent variation of the biological properties, for example the resistance of the tissue or organ element, which changes during the electroporation process. The desired parameters input by the user comprises duration, interval and peak voltage of the arbitrary waveform pulsing train. Hereinafter, these parameters are referred as "operation parameters".

A micro-controller unit 3 is coupled to the control module 4 via a signal line 21, wherein the micro-controller unit will receive and store the operation parameters from the control module in order to control and synchronize the arbitrary waveform generator unit 2 and customized power module 1 in either constant voltage and/or constant current operation modes. During the constant voltage operation mode, a fixed voltage is applied to the tissue or cell while the current is allowed to vary for the range of operation parameters. Vice versa, in constant current operation mode, the current is maintained across the target media and the voltage is allowed to vary for the range of operation parameters. These two operation modes provide the present invention with the versatility to adapt to the various biological properties of the target media. In one embodiment, the micro-controller unit 3 may consist of a PIC 16F876 microchip processor accompanied by suitable memory modules.

Both the arbitrary waveform generator unit 2 and customized power module 1 are coupled to the micro-controller unit via control/signal lines 21. The switch unit 8 is coupled to the micro-controller unit 3 to provide a means for the user to initiate the electroporation process. One preferred embodiment of the arbitrary waveform generator unit 2 is the Agilent 33220A 20 Mhz Arbitrary Waveform Generator that can produce any patterns of arbitrary waveform pulsing train specified by the user. The Agilent IntuiLink Arbitrary Waveform software, referred herein as "waveform editor", is implemented in the control module 4 to allow the user to create any arbitrary waveform pulsing train through the mouse or touch screen manipulation. The arbitrary waveform pulsing train will then be transferred and stored in the arbitrary waveform generator unit 2. When the switch unit 8 is activated, the micro-controller 3 will instruct the arbitrary waveform generator 2 to reproduce the stored arbitrary waveform pulsing train to the customized power module 1.

Figure 2:
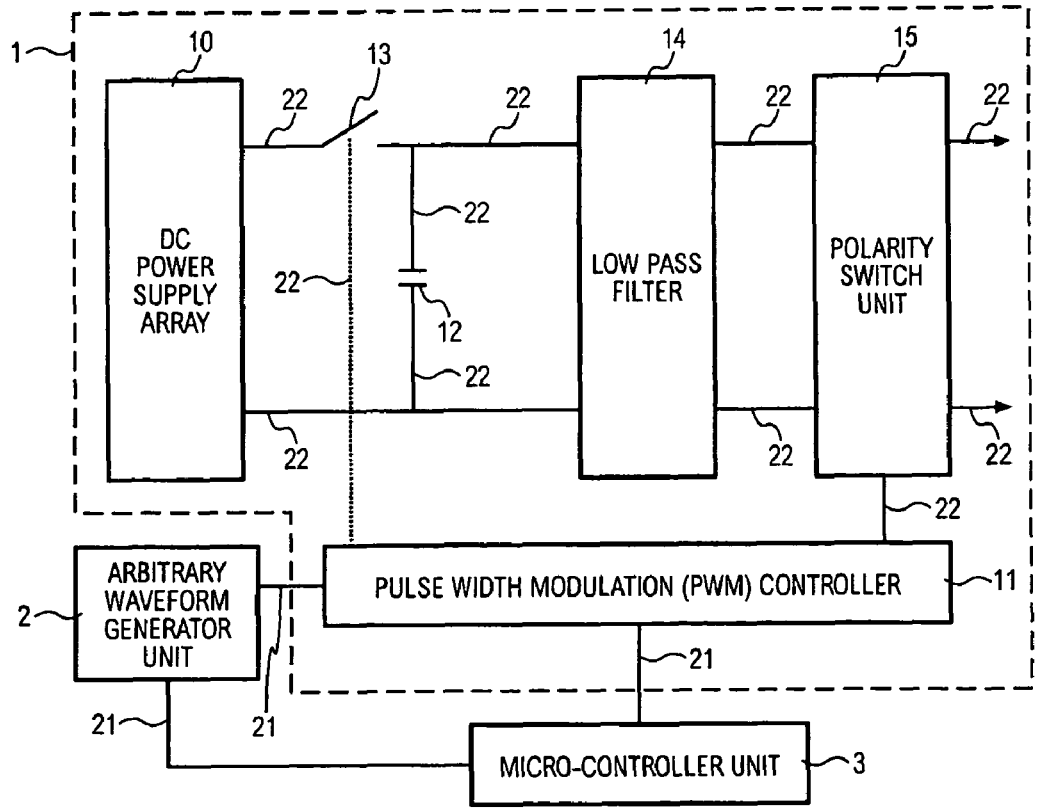
FIG. 2 illustrates a block diagram of the apparatus for applying electric fields across a target media.

The customized power module 1 will now be described. FIG. 2 illustrates the schematics of a customized power module 1 for amplification of the arbitrary waveform pulsing trains generated by the arbitrary waveform generator unit 2. In a preferred embodiment, a pulse width modulation (PWM) controller 11 comprising of a combination of electronic components is coupled to the arbitrary waveform generator unit 2 and the micro-controller unit 3 via control/signal lines 21. The PWM controller 11 receives and processes the waveform signals and command signals from the arbitrary waveform generator unit 2 and micro-controller unit 3 respectively, in order to control the operation of an electronic switch 13, for example a transistor. The electronic switch 13, coupled to a direct current (DC) power supply array 10, provides the means for the PWM controller 11 to control the output voltage delivered from the DC power supply array to a capacitor 12. The preferable capacitor value range is 330 μF to 2200 μF with corresponding operating voltage levels of 250V and 5 kV respectively. The DC power supply array 10 may comprise a plurality of conventional power supplies that can provide a wide range of voltages up to 5 kV required for the electroporation process.

During operation, switching of the electronic switches 13 creates high frequency spikes that are deleterious to the application of electroporation on the target media 30. A low pass filter (LPF) 14 is coupled to the capacitor 12 to remove any undesirable frequency spikes. The capacitor 12 delivers an output waveform pulsing train to the LPF 14, whereby the LPF removes the undesired frequency spikes in the output waveform pulsing train and generates a filtered waveform pulsing train. One embodiment of the low pass filter is a combination of resistors and capacitors with an operating range of 1 μF to 10 μF.

The filtered waveform pulsing trains only comprises positive pulses. In order to substantially replicate the arbitrary waveform pulsing train produced from the arbitrary waveform generator unit 2, a polarity switch unit 15 is utilized to reverse the polarity in the pulses of the filtered arbitrary waveform pulsing train. The PWM controller 11 is coupled to the polarity switch unit 15 to control the required pulses of the filtered waveform pulsing train to be reversed. Thereafter, the polarity switch unit 15 produces an amplified waveform pulsing train that substantially corresponds to the arbitrary waveform pulsing train delivered by the arbitrary waveform generator unit 2. The polarity switch unit comprises a combination of transistors. All the individual components 10, 11, 12, 13, 14, 15 are inter-coupled by electric conductors 22 as illustrated in FIG. 2.

The customized power module 1 is capable of operation in constant voltage and/or constant current operation modes, as was discussed hereinabove. When operating at the constant voltage mode in a low voltage range of 0V to 250V, the customized power module 1 can deliver a current range up to 110 A for pulse duration of 100 ms to 1 s. Similarly, in high voltage range of 250V to 5 kV, it can provide a current range up to 250 A for a pulse duration of 10 μs to 200 μs. Alternatively, in the constant current mode, the range of current is between 0 A to 0.25 A with a pulse duration of 0 s to 30 s. During this mode, the voltage provided by the customized power module 1 is not controlled and is dependent on the biological properties of the target media.

Electrodes 5 are coupled to the output of the customized power module 1 via electric conductors 22, wherein the electrodes transform the arbitrary waveform pulsing train generated by the customized power module into electric fields that are to be applied across the target media 30. In one embodiment, the electrodes 5 are tweezers made from surgical grade stainless steel. During the electroporation process, at least two electrodes 5 are utilized to produce an electric field across the target media 30. These tweezers electrodes may consist of a series of interchangeable tips of various geometry, shapes and sizes that enables in vivo or ex vivo electroporation on live animal organs, for example mouse liver and muscles.

During the electroporation process, a contactless remote high speed sensory module 6 is implemented to monitor, measure and record the temperature distribution of the target media 30. In one embodiment, the sensory module 6 may comprise an infra-red (IR) sensory module housing a series of customized lens and utilizing a laser pointer device to guide the sensory module to the specified area of the target media 30. This enables the study of the thermal effect relationship with respect to the user configured arbitrary waveform pulsing train and tissue damage.

A measurement unit 7 utilizes a set of probes 23 to monitor, measure and record all information from the target media 30. These information including waveforms, voltage, current and tissue/cell resistance during the initial, transient and final conditions of the electroporation process can be uploaded to the control module 4 for further process analysis and optimization. One preferred embodiment of the measurement unit 7 is the Agilent Oscilloscope 54624A. Waveforms from the oscilloscope can be stored in any portable storage media such as floppy disk, thumb drive, MMC/SD/CF memory cards or printed out directly through an attached printer.

Figure 3:
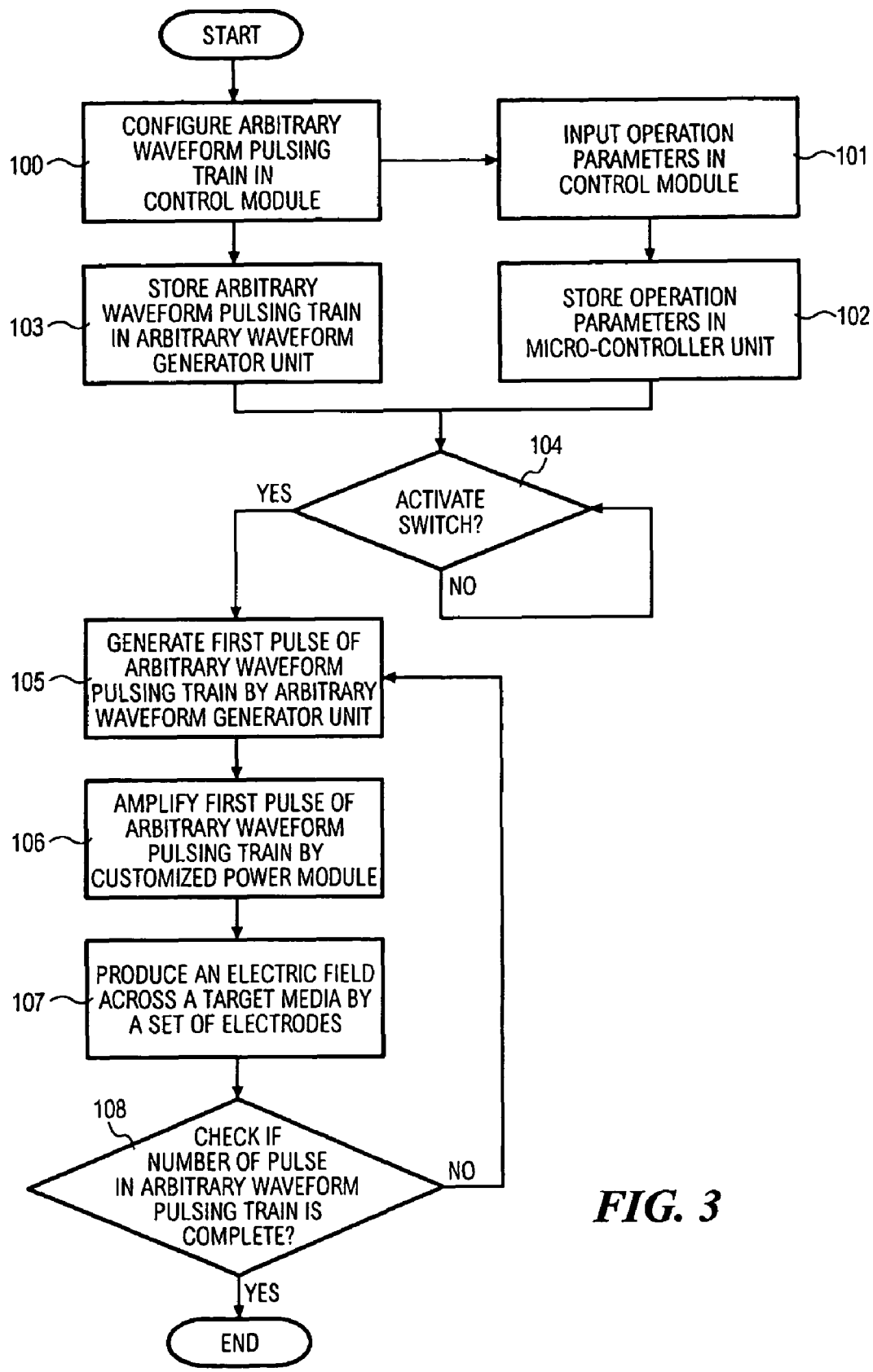
FIG. 3 illustrates the flowchart describing the operation procedures of the present invention.

The operation procedures of the apparatus will now be described from the flowchart shown in FIG. 3. Before the electroporation process is initiated, the user uses the control module 4 to configure the arbitrary waveform pulsing train 100. After the arbitrary waveform pulsing train is configured, the user inputs into the control module 4 all other operation parameters 101. The operation parameters entered into the control module 4 are downloaded and stored into the memory of micro-controller unit 3 for subsequent processing 102. At the same time, the user configured arbitrary waveform pulsing train is downloaded to the memory of arbitrary waveform generator unit 2 for subsequent processing 103.

Once the switch unit 8 is activated 104, the actual electroporation process starts. The arbitrary waveform generator unit 2 is activated for the first programmed pulse duration by the micro-controller unit 3, wherein the arbitrary waveform generator unit 2 outputs the first programmed pulse of the user configured arbitrary waveform pulsing train 105. The customized power module 1 then receives and amplifies the first pulse accordingly to the appropriate voltage levels 106.

When the amplified pulse from the customized power module 1 is output to the electrodes 5, an electric field is created 107 at the target media 30. Before the first pulse is completed, the micro-controller 3 computes and checks whether the programmed number of pulses is completed 108. If the user has specified more than one pulse, the micro-controller unit 3 repeats activation of the arbitrary waveform generator unit 2 to generate the second pulse and its subsequent pulses 105. This process continues on until the total number of pulses for a particular pulse train programmed by the user is completed. If only one pulse is specified or when the number of pulses of the user configured arbitrary waveform pulsing train is completed, the micro-controller unit 3 will terminate the electroporation process 109.

During the electroporation process, the measurement unit 7 constantly monitors and records all information including transient operating conditions including waveform voltage, current and cell/tissues resistance. Concurrently, the sensory module 6 monitors and records the temperature distribution of the target media 30 during the entire electroporation process.

While the present invention has been described with reference to particular embodiments, it will be understood that the embodiments are purely illustrative and that the invention scope is not so limited. Alternative embodiments of the present invention will become apparent to those having ordinary skill in the art to which the present invention pertains. Such alternate embodiments are considered to be encompassed within the spirit and scope of the present invention. Accordingly, the scope of the present invention is described by the appended claims and is supported by the foregoing description.

What is claimed is:

1. An apparatus for generating arbitrary waveform pulsing trains for an electroporation process, said apparatus comprising of:
   a customized power module including:
     a direct current (DC) power supply array for providing an output voltage;
     a capacitor;
     an electronic switch coupled to the DC power supply array, wherein the electronic switch provides means for controlling the output voltage from the DC power supply array to the capacitor;

a pulse width modulation (PWM) controller coupled to the electronic switch, wherein the PWM controller receives an arbitrary waveform pulsing train and command signals for controlling the electronic switch;

a low pass filter (LPF) coupled to the capacitor, wherein the LPF receives an output waveform pulsing train from the capacitor and removes high frequency spikes in the output waveform pulsing train from the capacitor, producing a filtered waveform pulsing train;

a polarity switch unit coupled to the low pass filter, wherein the polarity switch unit reverses the polarity of the required pulses in the filtered waveform pulsing train to produce an amplified waveform pulsing train;

a waveform generator unit coupled to the customized power module, wherein the waveform generator unit provides the arbitrary waveform pulsing train to the customized power module; wherein the amplified waveform pulsing train produced by the polarity switch unit substantially corresponds to the arbitrary waveform pulsing train; and a sensory module, wherein the sensory module includes a laser pointer device that locates the target media for temperature measurement undergoing the electroporation process.

2. The apparatus as claimed in claim 1 further comprising of a micro-controller unit coupled to the PWM controller and arbitrary waveform generator unit, wherein the micro-controller unit controls the PWM controller in switching of the electronic switch.

3. The apparatus as claimed in claim 1 further comprising of a control module, wherein the control module allows the user to configure the arbitrary waveform pulsing train and input operation parameters.

4. The apparatus as claimed in claim 3, wherein the operation parameters can include the pulse strength, pulse duration and pulse frequency of the arbitrary waveform pulsing train.

5. The apparatus as claimed in claim 1 further comprising at least two electrodes coupled to the customized power module, wherein the at least two electrodes transforms the desired waveform pulsing train from the polarity switch unit into an electric field across a target media during electroporation.

6. The apparatus as claimed in claim 5 further comprising a set of tweezer electrodes, wherein the tweezer electrodes consist of a set of interchangeable tips, wherein interchangeable tips comprised of various shapes and sizes.

7. The apparatus as claimed in claim 1 further comprising of a measurement unit that is coupled to the customized power module and the target media.

* * * * *